United States Patent [19]
Kreidler et al.

[11] Patent Number: 5,520,181
[45] Date of Patent: May 28, 1996

[54] POSITIONING DEVICE FOR PRODUCING MOVEMENT IN THE SHOULDER

[75] Inventors: Marc S. Kreidler, Sunnyvale, Calif.; Rodney E. Bell, Kalamazoo, Mich.; Charles P. Ho, Palo Alto, Calif.; David T. H. Hung, Palo Alto, Calif.; Erin A. Ryan, Palo Alto, Calif.; Harrie J. M. Wolters, Menlo Park, Calif.; Chuckson M. Yokota, Fremont, Calif.

[73] Assignee: Technology Funding Secured Investors II, San Mateo, Calif.

[21] Appl. No.: 157,475

[22] Filed: Nov. 24, 1993

[51] Int. Cl.⁶ ............................................ A61B 5/055
[52] U.S. Cl. .......................... 128/653.5; 5/601; 5/623
[58] Field of Search .................. 128/653.2, 653.5, 128/774, 782, 878; 601/33; 5/601, 623, 646, 647

[56] References Cited

U.S. PATENT DOCUMENTS

| | | | |
|---|---|---|---|
| 541,863 | 7/1895 | Loomis | 5/623 |
| 3,020,909 | 2/1962 | Stevens | 5/623 |
| 4,651,719 | 3/1987 | Funk et al. | 601/33 |
| 4,669,451 | 6/1987 | Blauth et al. | 601/33 |
| 4,698,837 | 10/1987 | Van Steenburg | 5/601 |
| 4,827,496 | 5/1989 | Cheney | 5/601 |
| 5,085,219 | 2/1992 | Ortendahl et al. | 128/653.5 |
| 5,329,924 | 7/1994 | Bonutti | 128/653.2 |
| 5,343,580 | 9/1994 | Bonutti | 5/601 |
| 5,427,116 | 6/1995 | Noone | 128/774 |
| 5,445,152 | 8/1995 | Bell | 128/653.5 |

FOREIGN PATENT DOCUMENTS 1569010  6/1990  U.S.S.R. .................. 601/33

OTHER PUBLICATIONS

Poppen et al., "Normal and Abnormal Motion of the Shoulder," *The Journal of Bone and Joint Surgery*, 58-A, No. 2; pp. 195–201, Mar. 1976.

Freedman et al., "Abduction of the Arm in the Scapular Plane: Scapular and Glenohumeral Movements," *The Journal of Bone and Joint Surgery*, 48-A, No. 8, pp. 1503–1510, Dec. 1966.

Howell et al., "Normal and Abnormal Mechanics of the Glenohumeral Joint in the Horizontal Plane," *The Journal of Bone and Joint Surgery*, 70-A, No. 2, pp. 227–232, Mar. 1976.

*Primary Examiner*—Joe Cheng
*Assistant Examiner*—Jeanne M. Clark
*Attorney, Agent, or Firm*—Flehr, Hohbach, Test, Albritton & Herbert

[57] ABSTRACT

A positioning device for producing movement in the shoulder of a human patient in MRI apparatus includes a base movable into the aperture of the MRI apparatus. On the base is provided a swivel which includes a first lever pivoted on an axis, on which the shoulder is located, in substantially the plane of the base. And then with the elbow in an elbow cup located at the end of the first lever arm, a second lever arm is pivoted at the cup. The second lever arm at its distal end restrains the forearm or hand of the patient. Movement of this second lever arm is sensed by an angle encoder mounted on the axis of the elbow cup to indicate internal/external rotation. Movement of the first lever arm is sensed by an angle encoder at the first axis to provide abduction/adduction angle movement information. Flexion/extension movement is also provided.

10 Claims, 8 Drawing Sheets

POSITIONING DEVICE FOR PRODUCING MOVEMENT IN THE SHOULDER

The present invention is directed to a positioning device for producing movement in the shoulder, and more specifically in a shoulder being examined in a magnetic resonance imaging (MRI) apparatus, and where a cinematic video tape is produced.

BACKGROUND OF THE INVENTION

MRI imaging of the shoulder has been done before, generally by manual manipulation. Because the shoulder is such a complex joint, static MRI images do not provide sufficient information, especially as to shoulder instability and impingement. One of the difficulties in manipulating the shoulder is the complexity of the joint itself, and the fact that it has many different types of movement, such as abduction/adduction (FIG. 5A); internal/external rotation (FIG. 5B), and flexion/extension movement (FIG. 5C). These movements may be defined as follows:

| | |
|---|---|
| abduction/adduction: | swing humerus up and down (up and down relative to person standing up) abduction - start with humerus pointing towards inferior of torso and swing upwards towards head (towards superior) adduction - start with humerus at abducted position and swing down to inferior of torso |
| internal/external rotation: | rotate along axis of humerus clockwise and counter-clockwise |
| flexion/extension: | swing humerus in plane orthogonal to torso flexion - swing humerus towards front (anterior of torso) extension - swing humerus towards back (posterior) of torso. |

During the MRI examination which may take some extensive period of time due to the necessity of acquiring several "slices" of the shoulder, the patient when inside of the aperture of the MRI apparatus must be made as comfortable as possible. At the same time, a positioning device is useful to allow for ease of incremental movement of the shoulder and to discriminate between types of movement as outlined above. The shoulder, of course, should be maintained in substantially the same physical location during the acquisition of the several images so that an effective cinematic video tape can be produced; in other words, the shoulder should be held and not necessarily restrained in a comfortable and repeatable position. In prior positioning techniques, even in the case of X-rays, manual manipulation was used.

OBJECT AND SUMMARY OF THE INVENTION

It is a general object of the present invention to provide a positioning device for producing movement in the shoulder of a human patient.

In accordance with the above object, there is provided a positioning device for producing movement in the shoulder of a human patient and its associated arm which includes the upper arm attached to the shoulder, the elbow and the forearm with a hand. The movement includes at least one of the following—abduction/adduction, internal/external rotation, and flexion/extension. It includes a base in the aperture of a magnetic resonance imaging (MRI) apparatus for carrying at least one shoulder of the patient into an imaging volume of the MRI apparatus.

Swivel means mounted on the base maintains such shoulder in substantially a fixed location in the imaging volume while allowing the associated arm to move to provide the shoulder movement, including a first axis around which the arm swivels, at which the shoulder is positioned. The swivel means includes a first lever arm mounted for rotation at one end around the axis and includes guide means for maintaining the shoulder in the imaging volume.

DESCRIPTION OF A PREFERRED EMBODIMENT

Figure 1:
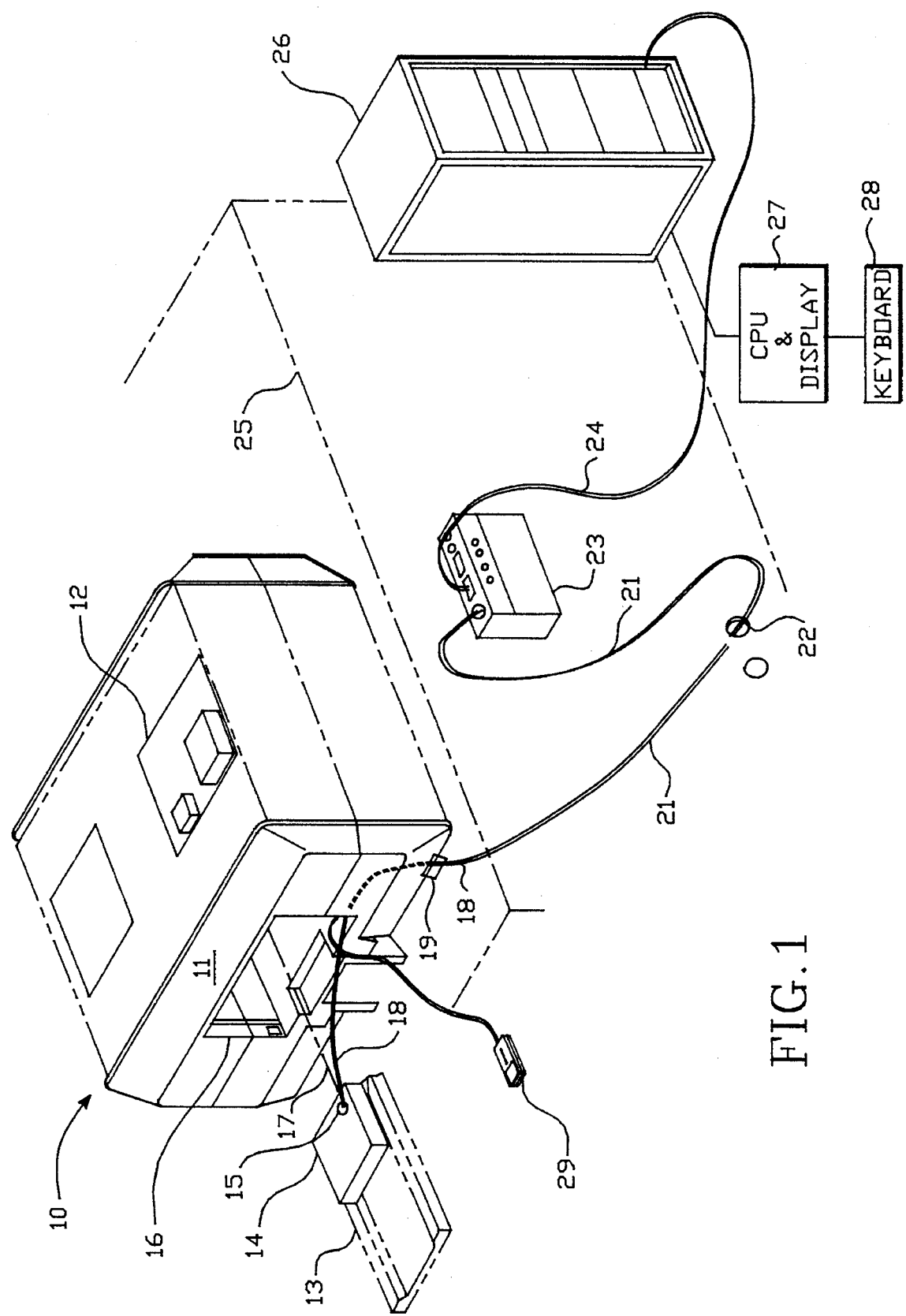
FIG. 1 is a simplified perspective view of an MRI apparatus in which the present invention is utilized.

FIG. 1 is a perspective view of MRI apparatus 10 which includes a magnet 11 and equipment designated at 12 to provide necessary radio frequency signals for the well known technique of MRI imaging. The body of the patient (not shown) is placed upon a sled 13 generally with the patient on his back in a supine position. On the sled is an orthopedic positioning device 14 with at least one angle encoder 15. The sled is moved into the aperture 16 indicated by the broken line 17, and imaging takes place.

As described in a copending application entitled "Automated Angle Encoder System for MRI Apparatus", Ser. No. 08/157,389, filed Nov. 23, 1993, and assigned to the present Assignee, an essentially nonmagnetic, nonmetallic cable 18 is connected to the angle encoder (which is described in detail in the above copending application) and through a coupling 19 to a longer cable 21 extending through an aperture 22 in the wall of a screening room 25. The screening room contains the MRI apparatus and its magnetic fields in a manner well known in the art. Cable 21 terminates in an electronics cabinet 23 which decodes the light pulse information, as described in the copending application, of the angle encoder 15 and converts it to a standard electronic digital code. Such code is transmitted to the equipment rack 26 by cable 24 and then to a central processing unit (CPU) and display 27 having a keyboard input 28. On that display the various MRI slices can be displayed and linked to form a cinematic video tape of the shoulder movement.

And on this tape are displayed the angles related to the various positions through which the shoulder is moved. Control unit 29 is used to start scans in the screening room.

Figure 2:
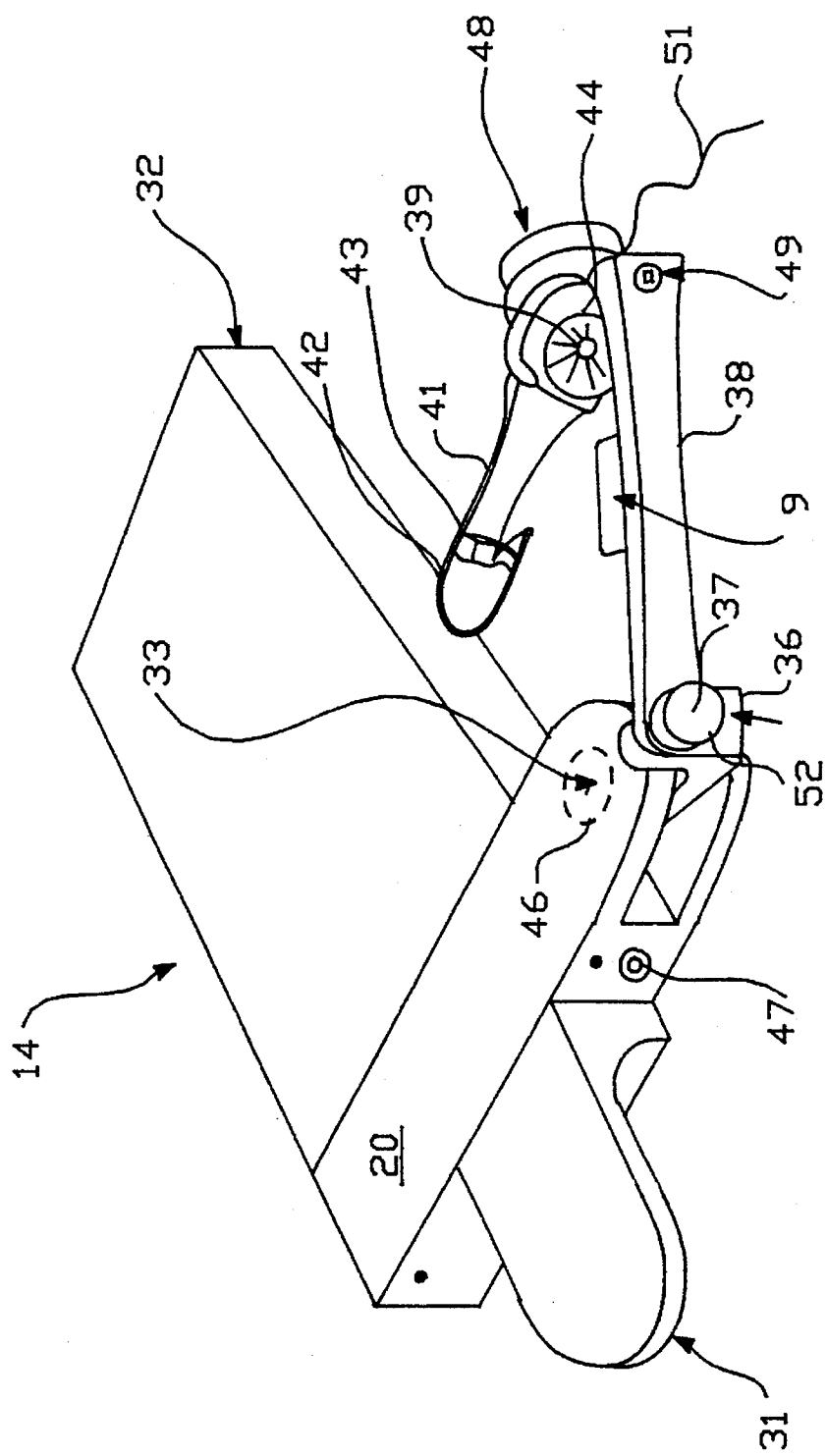
FIG. 2 is a perspective view of positioning apparatus showing one embodiment of the present invention.

FIG. 2 illustrates a positioning device 14 for the shoulder which is placed on the sliding platform or sled 13. It includes a head rest module 31 and a back rest module 32 (on which the patient is in a supine position) both fastened to a base unit 20. As illustrated, thus the right shoulder would be in the position indicated by the center point or axis 33 in unit 20. All of the parts of the positioning unit are of course nonmagnetic and substantially nonmetallic.

Figure 5A:
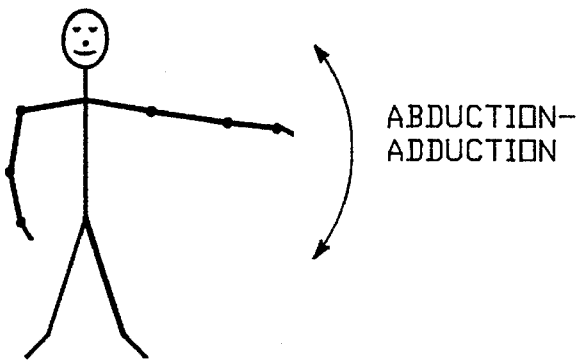
FIGS. 5A–5C are illustrations of three different shoulder movements.
Figure 5B:
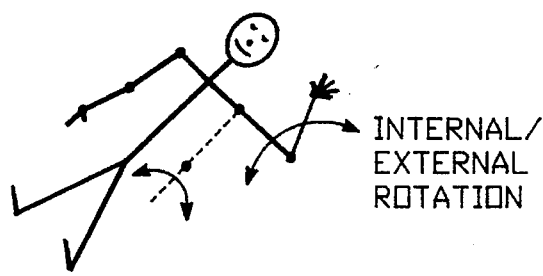
Figure 5C:
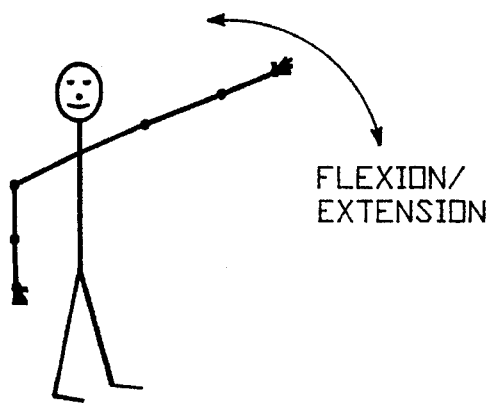

Pivoted on the axis 33 are swivel means which are mounted on the base unit 20 and which hold the shoulder substantially at the axis 33 in the imaging volume but allows the arm and its associated hand to move in an abduction/adduction mode, an internal/external rotation mode or in flexion/extension (see FIGS. 5A–5C). Such swiveling device includes a first lever arm which in the embodiment of FIG. 2 includes a first portion 36 which has one end pivoted at axis 33 for movement about the axis 33. A restraining strap 9 may be used for the upper arm. Then connected on an axis 37 is a second portion 38 which again generally follows the movement of the first portion 36.

Figure 6:
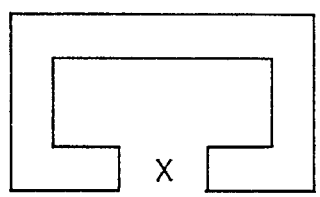
FIG. 6 is a simplified plan view of an alternate MRI magnet.

At the other end of the lever portion 38 on a pivot point or second axis 39 is a second lever arm 41 which has a distal end 42. It has a forearm restraint which may be merely a Velcro strap 43 for holding the wrist and forearm to the lever 41. Then the bent elbow of the arm is held in an elbow cup 44 mounted at the pivot point 39 and affixed to the other end of the arm portion 38. When the right shoulder (not shown; but see FIGS. 5A–5C) is at the first axis 33 and the elbow in the elbow cup 44 and the wrist or hand affixed by strap 43 to the distal end 42, the patient may freely move his shoulder in three modes:

1. In an abduction/adduction mode (see FIG. 5A), arm portions 36 and 38 of the first lever arm are pivoted around point 33; thus the patient as discussed above brings his hand and forearm in front of the chest and then the opposite movement. Because of the limited aperture space, the elbow must be bent. But if a "C" type magnet is used as shown in FIG. 6 then the arm can be straight as in FIG. 5A. Thus an elbow cup 44 would not be necessary. To record the angles of this movement, there is mounted, as shown by the dashed line 46, an angle encoder 15 (see FIG. 1). If precise incremental movement (viz., kinematic) is desired then a drive socket 47 will drive through a simple worm gear arrangement (not shown) the arm portion 36 to various incremental precise positions. Thus this will enable the creation of a cinematic film of the shoulder moving in the abduction/adduction mode. At the same time because of the structure of the swiveling means which restrains the elbow and the forearm, the shoulder is maintained in substantially the same imaging position to thus provide a good quality series of repeatable images.

If dynamic or continuous slow movement is desired the gear arrangement is disabled.

2. Where internal/external rotation movement of the shoulder is desired (see FIG. 5B), the rotation around axis 33 is minimal with the main rotation being about the axis 39. Here the forearm, the elbow and the elbow cup 44 is pivoted in a plane substantially perpendicular to base unit 20 to provide internal/external rotation motion. To measure the angle of that motion is an encoder 48 mounted on the axis 39. To provide for precise incremental movement as in the case of the drive socket 47, a drive socket 49 is provided in arm portion 38. Finally the fiber optic cable 51 extends from the encoder 48 which is effectively the cable 18 illustrated in FIG. 1.

3. At axis 37 there is also a control knob 52 which can fix the slant angle of the arm 38 to provide for proper flexion/extension (see FIG. 5C).

Figure 3:
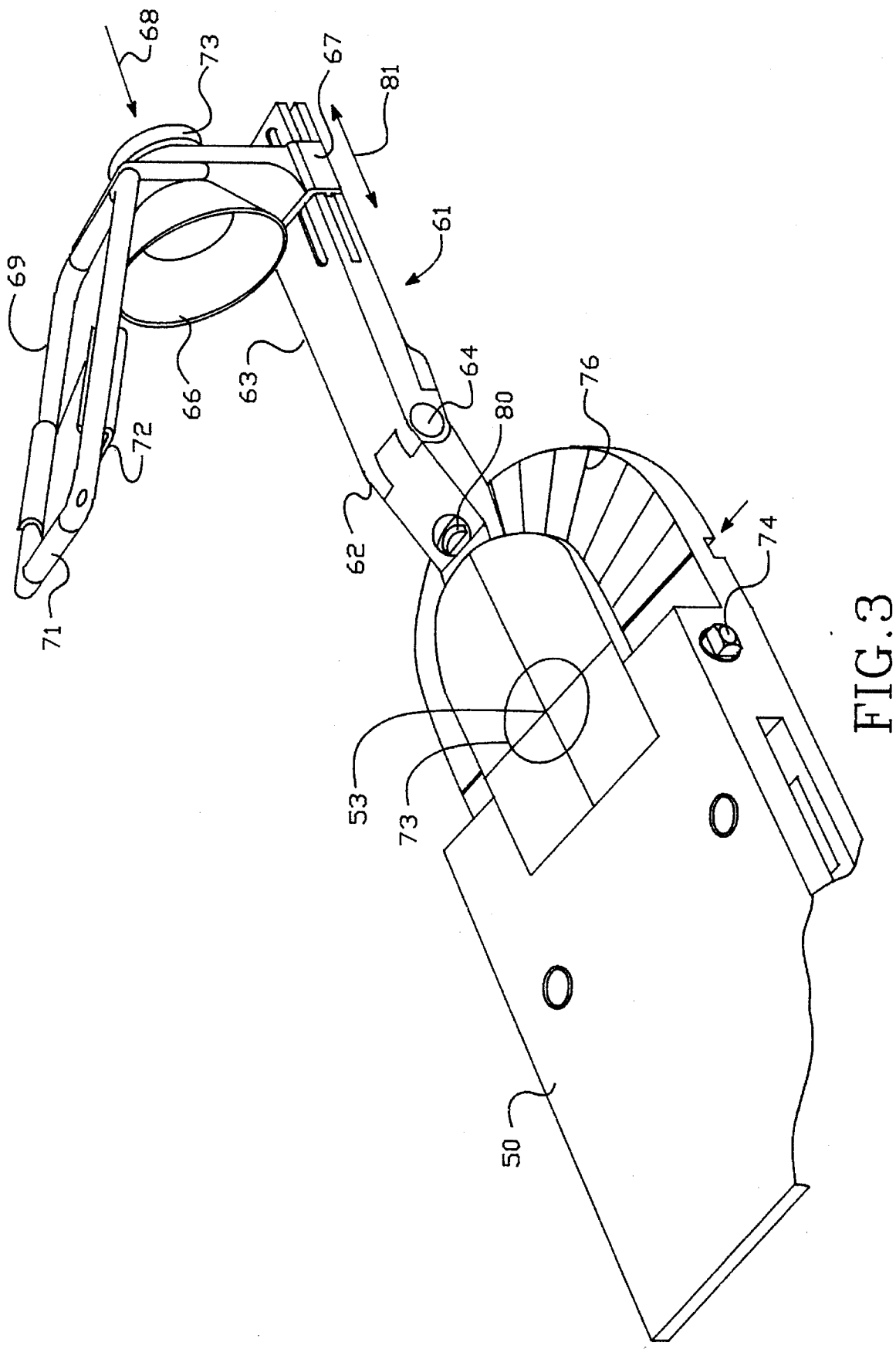
FIG. 3 is a perspective view of positioning apparatus showing another embodiment of the invention.
Figure 4:
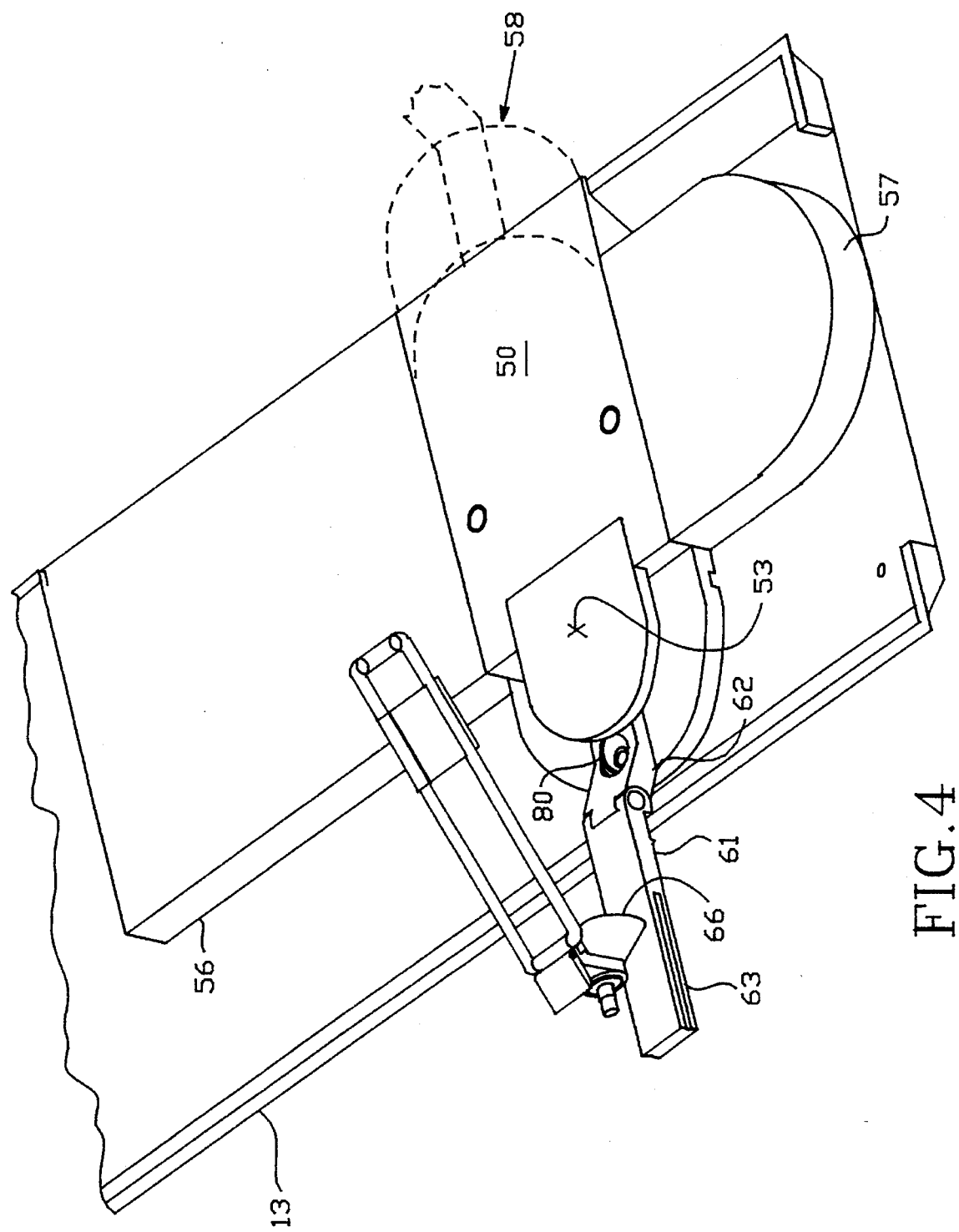
FIG. 4 is a perspective view of the apparatus of FIG. 3 showing its location on the sliding table of MRI apparatus and illustrating its reversibility for the left and right shoulders.

FIGS. 3 and 4 illustrate another embodiment of a shoulder positioning device. Referring to both figures, the shoulder is effectively positioned at an axis 53. As more clearly illustrated in FIG. 4, the back rest 56 is attached to a base unit 50 affixed to the movable sled (see FIG. 1). Also as illustrated in FIG. 4, is a headrest portion 57. Thus with the patient in a supine position, the left shoulder would be located at the axis 53. Moreover as indicated by the dashed lines 58, the entire apparatus may be switched to the other side of base unit 50 so that the right shoulder is imaged.

For all of the foregoing the shoulder has wrapped around it, a radio frequency coil which generates both a radio frequency pulse and receives the resultant MRI signal. Such coils are well known.

The alternative positioning device of FIGS. 3 and 4 includes a lever arm 61 which, as in the case of the other embodiment, has a first portion 62 and a second portion 63 which are pivoted together at an axis 64. At the end of the lever arm 61, is mounted on elbow cup 66 on a slidable extension 67 of the lever arm 61 shown by arrows 81. Such sliding action of extension 67 in the grooves of arm 63 provides for effective abduction/adduction movement (and also flexion/extension). The elbow cup is centered on the axis 68 which is a second axis (relative to the first axis 53) for a second lever arm 69. Arm 69 is of an elongated rectangular shape and includes a handhold 71 for the hand of the human patient and a slidable forearm limiting plate 72. This restrains the forearm, through the voluntary gripping of the patient, against the plate 72 and in close proximity to arm 69. Thus the lower arm 61 in combination with its other attachments guides the arm while maintaining the shoulder in the imaging volume. Located at axis 68 may be an encoder 73 which provides the angle of the internal/external rotation of the shoulder. Parenthetically, the same unit 73 may be located on the axis 53 to indicate abduction/adduction movement.

Finally as in the case of the embodiment of FIG. 2, precise incremental movement can be provided by, for example, the drive socket input at 74. This can be disabled by switch 80. Visual angle markers are provided at 76 to supplement the abduction readout of the encoder 73. The removability of encoder 73 is shown in the above copending application; it fits into its location on the various axes 53 or 68 merely by inserting a shaft in a socket and an appropriate pin connection keeps the casing from rotating. Alternatively permanent encoders may be mounted.

With the foregoing shoulder positioners of either embodiment (FIGS. 2 or 4) the shoulder is thus held but not restrained in a comfortable and repeatable position. The shoulder joint is unstressed and left in an anatomically natural condition. There is sufficient space for the radio frequency shoulder coil to move freely for the desired range of motion.

Rather than use a driven mode, dynamic scanning is available by a unilateral gear linkage (not shown) where the patient can accomplish movement himself. However, in the kinematic mode, movement may be halted every five degrees. The two lever arms of the device are rugged enough to support even the largest patient without significant deformation of structure. This increases the repeatability and therefore the efficacy of the device. The patient is positioned on his back with the shoulder centered in the imaging zone and with the hand positioned such that the thumb is pointed upward.

The present positioning device since it is intended for rotation of the shoulder, by its nature minimizes scapular motion. All movements, either abduction or rotation, are with the elbow bent. This minimizes volume consumed in the limited aperture of the MRI apparatus (but see the "C" magnet of FIG. 6) and also is more comfortable for the patient. Visual angular position readings are made-available as shown at 76 in FIG. 3 and the same can be provided for the rotation movement.

Figure 7A:
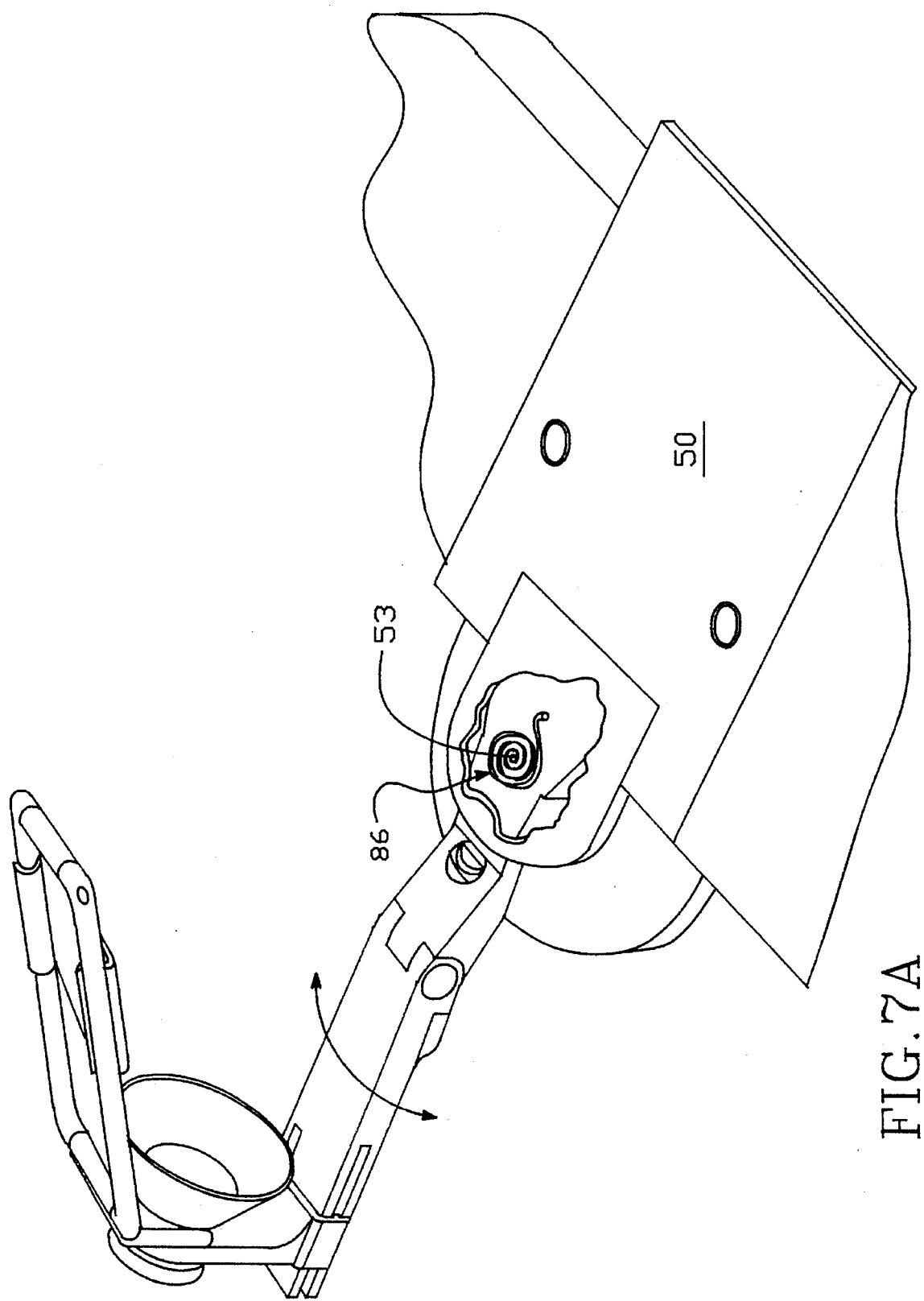
FIGS. 7A–7C are perspective views showing modifications to FIG. 3 and 4.
Figure 7B:
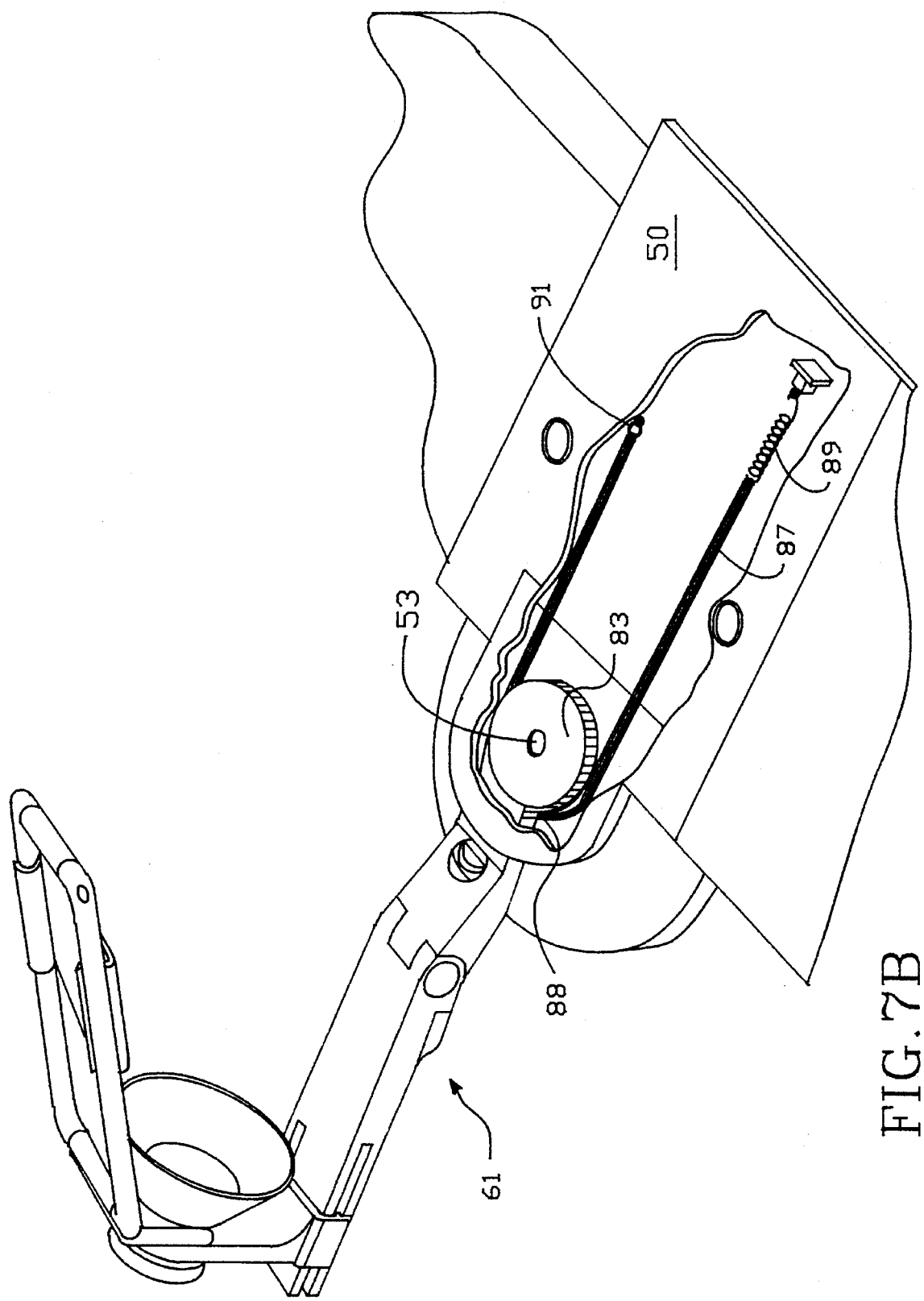
Figure 7C:
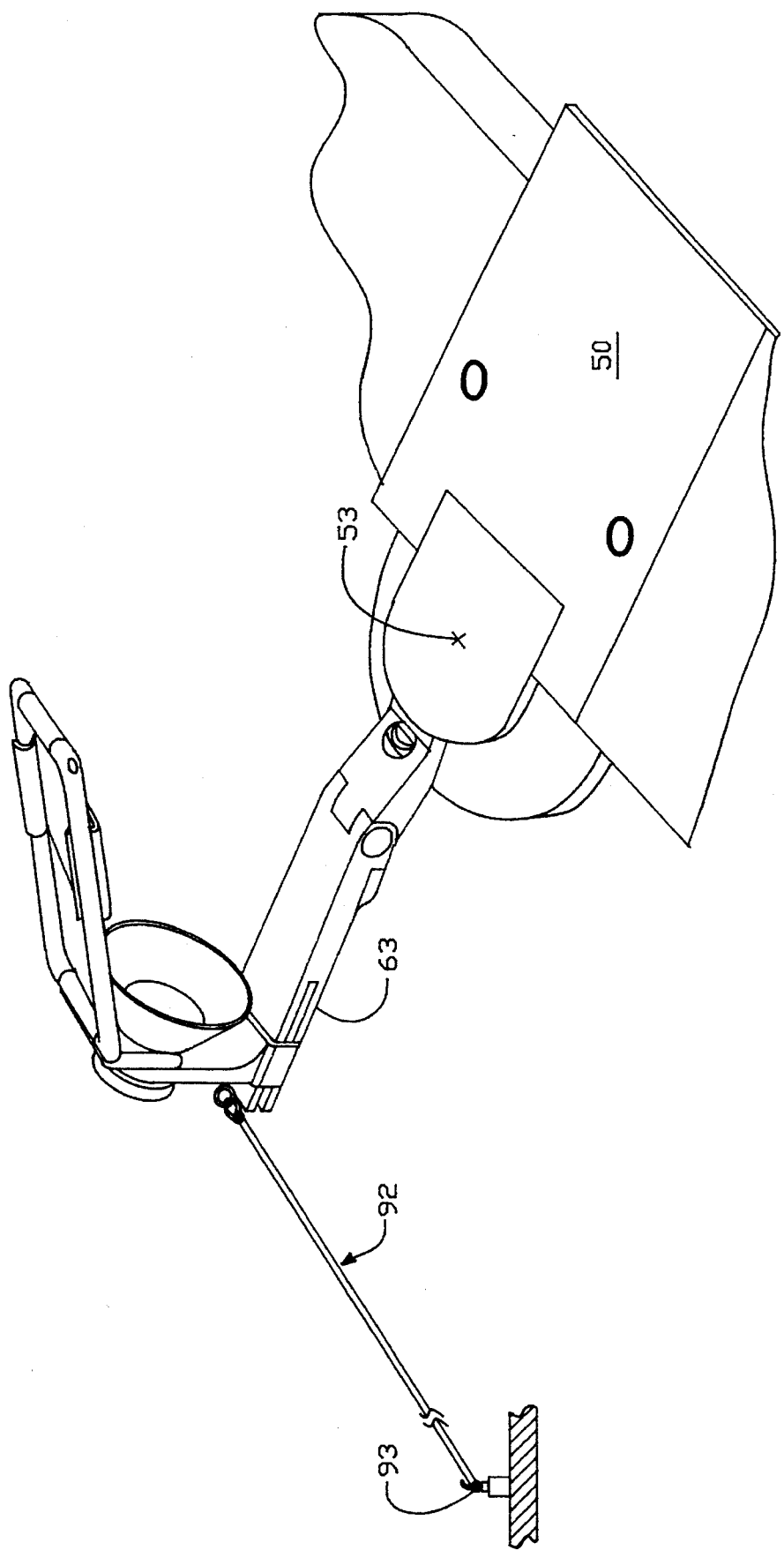

In some cases it is desired in one of the above movements to push against an external force. This can be provided by the following:

a) FIG. 7A—a nonmagnetic clock spring 86 around axis 53;

b) FIG. 7B—a drive belt 87 fastened to disk 83 at 88 and rotatable with lever 61 and biased by nonmagnetic springs 89, 91;

c) FIG. 7C—an elastomeric spring 92 between lever 63 and fixed point 93.

Thus a positioning device for producing movement of the shoulder has been provided.

What is claimed is:

1. A positioning device for use in combination with an MRI apparatus for producing movement in the shoulder of a human patient and its associated arm which includes the upper arm attached to the shoulder, the elbow and the forearm with a hand, said movement including abduction/adduction, and flexion/extension, said device comprising base means moveable in the aperture of the magnetic resonance imaging (MRI) apparatus for carrying at least one shoulder of the patient into an imaging volume of the MRI apparatus;

swivel means mounted on said base means for maintaining the shoulder in substantially a fixed location in the imaging volume while allowing the associated arm to move to provide the shoulder movement in at least two degrees of freedom, including a first axis around which the arm swivels at which the shoulder is positioned for performing abduction/adduction and a third axis perpendicular to the first axis for performing flexion/extension;

said swivel means including a first lever arm having two ends, mounted for rotation at one end around said axes and including means for guiding said arm for maintaining the shoulder in the imaging volume while producing either of the shoulder movements, such means for guiding including elbow cup means mounted at the other end of said first lever arm for receiving the elbow.

2. The device of claim 1 where external/internal rotation movement of the shoulder is provided by a second lever arm and including means for pivotally coupling said second lever arm at a second axis to said other end of said first lever arm and including means at the distal end of said second arm for restraining movement of the forearm.

3. A device as in claim 1 including angle encoder means mounted on said first axis for indicating the angle of said abduction/adduction.

4. A device as in claim 2 including an angle encoder means mounted on said second axis for indicating the angle of said internal/external rotation.

5. A device as in claim 2 wherein said means for restraining the forearm is a handhold at said distal end of said second lever arm and including an associated forearm limiting plate mounted on said second lever.

6. A device as in claims 3 or 4 where said angle encoder means is removably attached.

7. A device as in claim 1 including an external drive means centrally located about said first axis for rotating said first lever arm and providing precise incremental movement of the shoulder.

8. A device as in claim 1 where said first lever arm is rotatable substantially in or parallel to the plane of said base means to perform abduction/adduction movement.

9. A device as in claim 1 substantially consisting of nonmetallic, nonmagnetic materials.

10. A device as in claim 1 where said elbow cup means is slidably mounted to said first lever arm.

* * * * *